United States Patent
Johnson

(10) Patent No.: US 9,861,381 B2
(45) Date of Patent: Jan. 9, 2018

(54) REMOVABLE BATTERY CASING FOR SURGICAL INSTRUMENT

(71) Applicant: Ethicon Endo-Surgery, Inc., Cincinnati, OH (US)

(72) Inventor: Gregory W. Johnson, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 297 days.

(21) Appl. No.: 14/077,358

(22) Filed: Nov. 12, 2013

(65) Prior Publication Data

US 2015/0133979 A1    May 14, 2015

(51) Int. Cl.
    *A61B 17/32*    (2006.01)
    *A61B 17/00*    (2006.01)
    *A61B 90/00*    (2016.01)

(52) U.S. Cl.
    CPC .......... *A61B 17/320068* (2013.01); *A61B 17/320092* (2013.01); *A61B 2017/00017* (2013.01); *A61B 2017/0046* (2013.01); *A61B 2017/00725* (2013.01); *A61B 2017/00734* (2013.01); *A61B 2017/320072* (2013.01); *A61B 2017/320088* (2013.01); *A61B 2090/0814* (2016.02)

(58) Field of Classification Search
    CPC .... A61B 19/38; A61B 19/026; H01M 2/1094; H01M 2/1022
    See application file for complete search history.

(56) References Cited

U.S. PATENT DOCUMENTS

| | | |
|---|---|---|
| 5,322,055 A | 6/1994 | Davison et al. |
| 5,806,668 A | 9/1998 | Bixby |
| 5,873,873 A | 2/1999 | Smith et al. |
| 5,980,510 A | 11/1999 | Tsonton et al. |
| 6,022,363 A | 2/2000 | Walker et al. |
| 6,325,811 B1 | 12/2001 | Messerly |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |

(Continued)

FOREIGN PATENT DOCUMENTS

EP    2617379    7/2013

OTHER PUBLICATIONS

U.S. Appl. No. 13/657,553, filed Oct. 22, 2012.
(Continued)

*Primary Examiner* — Corrine McDermott
*Assistant Examiner* — Joshua Levine
(74) *Attorney, Agent, or Firm* — Frost Brown Todd LLC

(57) ABSTRACT

A surgical instrument includes a body, a grip, and a strip assembly. The strip assembly releasably couples the grip with the body. The grip is movable from a first position to a second position. The grip is coupled with the body in the first position and detached from at least a portion of the body in the second position. At least a portion of the strip assembly detaches from at least a portion of the grip, the body, or another portion of the strip assembly when the grip is in the second position.

12 Claims, 8 Drawing Sheets

(56) References Cited

U.S. PATENT DOCUMENTS

| | | | |
|---|---|---|---|
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,416,101 B2 | 8/2008 | Shelton, IV et al. | |
| 8,372,001 B2 * | 2/2013 | Akagi | A61B 1/04 361/679.57 |
| 8,453,914 B2 | 6/2013 | Laurent et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,657,174 B2 | 2/2014 | Yates et al. | |
| 8,663,262 B2 | 3/2014 | Deville et al. | |
| 8,939,974 B2 | 1/2015 | Boudreaux et al. | |
| 8,986,302 B2 | 3/2015 | Aldridge et al. | |
| 9,072,523 B2 | 7/2015 | Houser et al. | |
| 9,161,803 B2 | 10/2015 | Yates et al. | |
| 2003/0149424 A1 * | 8/2003 | Barlev | A61B 19/38 606/1 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0239012 A1 | 9/2009 | Thomasset et al. | |
| 2010/0069940 A1 | 3/2010 | Miller et al. | |
| 2012/0078243 A1 | 3/2012 | Worrell et al. | |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2013/0023868 A1 | 1/2013 | Worrell et al. | |
| 2013/0030428 A1 | 1/2013 | Worrell et al. | |
| 2013/0103023 A1 | 4/2013 | Monson et al. | |
| 2013/0289592 A1 | 10/2013 | Stulen et al. | |
| 2014/0005701 A1 | 1/2014 | Olson et al. | |

OTHER PUBLICATIONS

U.S. Appl. No. 13/716,308, filed Dec. 17, 2012.
U.S. Appl. No. 13/804,417, filed Mar. 14, 2013.
U.S. Appl. No. 61/410,603, filed Nov. 5, 2010.
International Search Report and Written Opinion re Application No. PCT/US2014/064988 dated Feb. 12, 2015.
European Communication dated Mar. 30, 2017 for Application No. EP 14806503.0, 5 pgs.

* cited by examiner

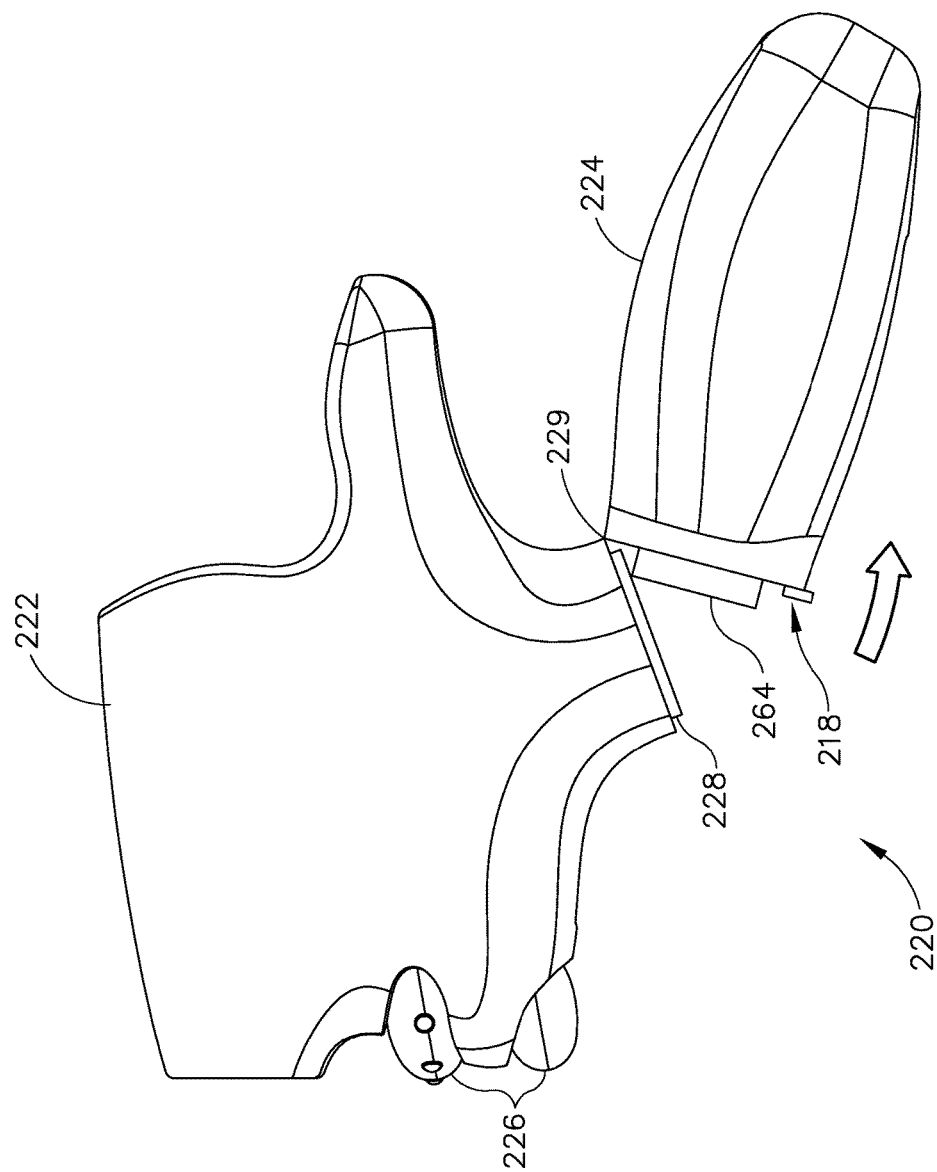

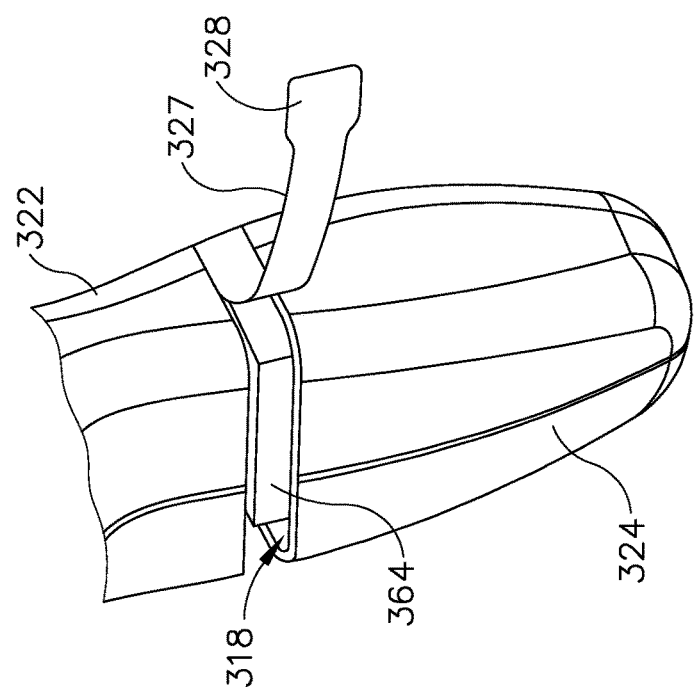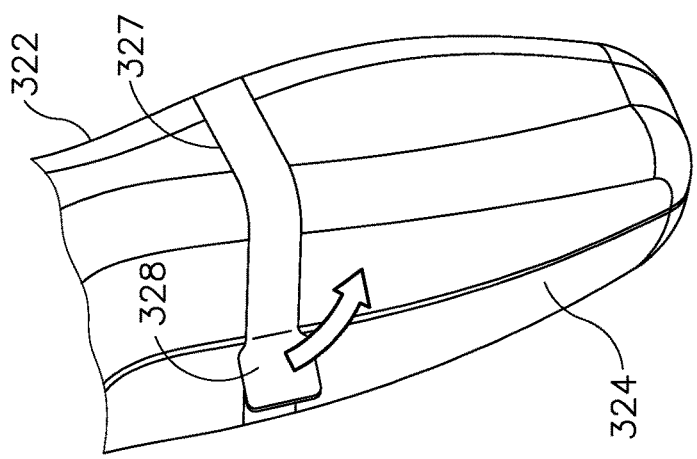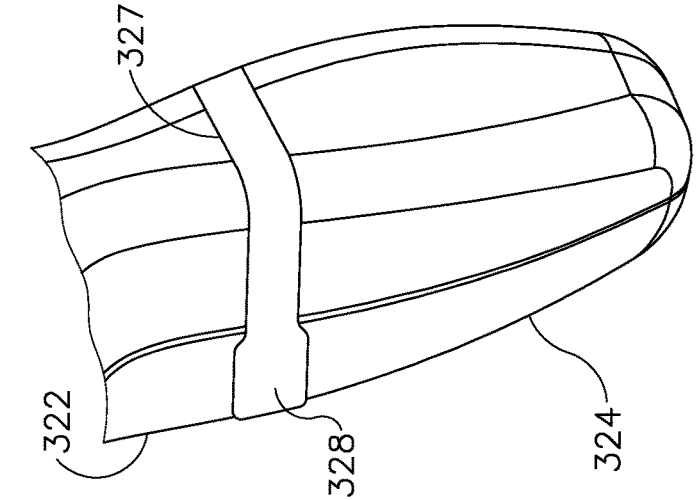

REMOVABLE BATTERY CASING FOR SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4B depicts a side elevational view of the handle assembly of FIG. 4A, pivoting the grip of the handle assembly;

FIG. 5A depicts a partial perspective view of another exemplary handle assembly for use with the instrument of FIG. 1;

FIG. 5B depicts a partial perspective view of the handle assembly of FIG. 5A, showing a tab being removed from the handle assembly; and FIG. 5C depicts a partial perspective view of the handle assembly of FIG. 5A, showing the tab further removed from the handle assembly.

Figure 1:
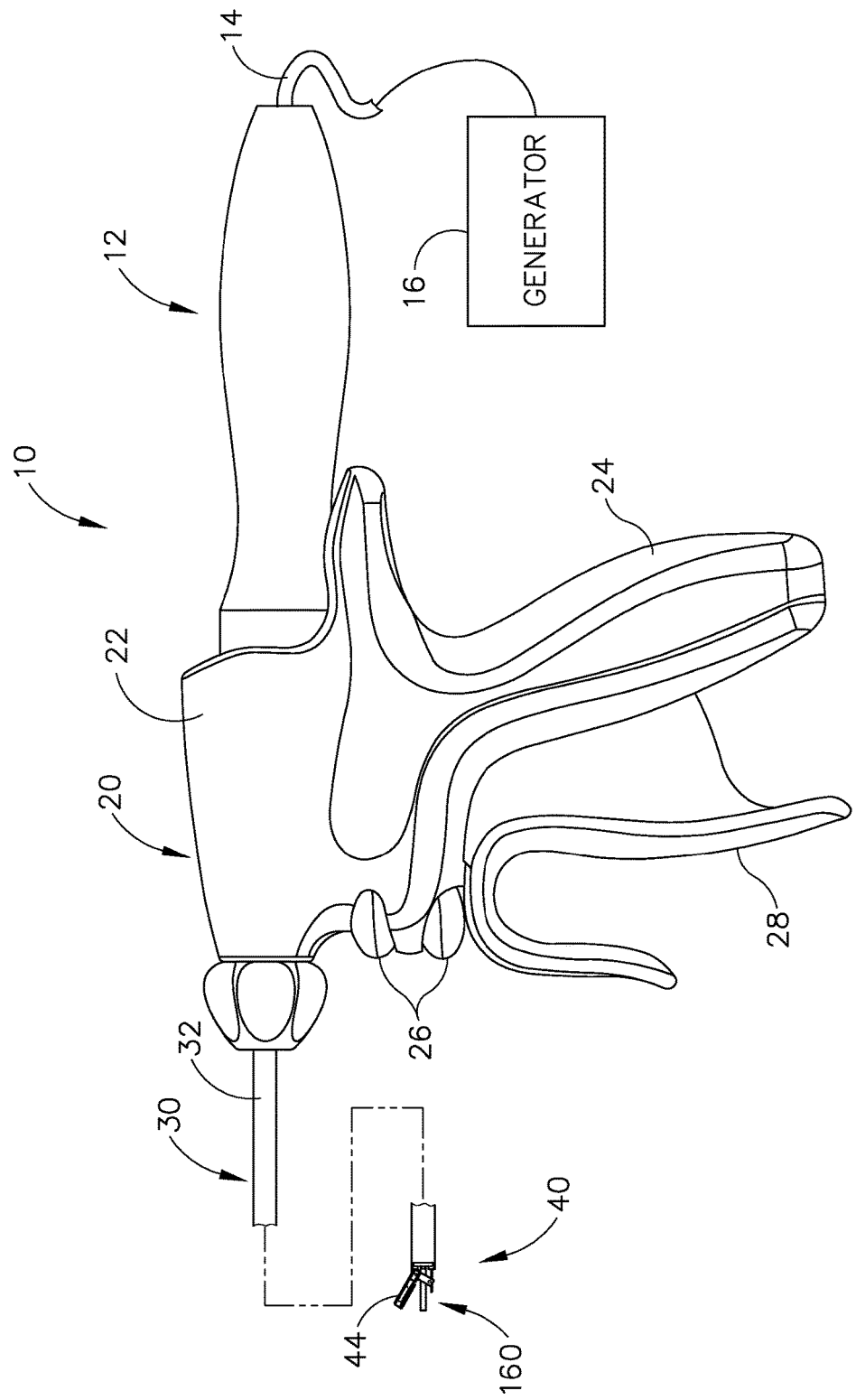
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750; U.S. Pub. No. 2010/0069940; U.S. Pub. No. 2011/0015660; U.S. Pub. No. 2012/0112687; U.S. Pub. No. 2012/0116265; U.S. patent application Ser. Nos. 13/538,588; 13/657,553; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

End effector (40) of the present example comprises clamp arm (44) and ultrasonic blade (160). Clamp arm (44)

includes a clamp pad that is secured to the underside of clamp arm (44), facing blade (160). Clamp arm (44) is operable to selectively pivot toward and away from blade (160) to selectively clamp tissue between clamp arm (44) and blade (160) in response to pivoting of trigger (28) toward pistol grip (24). Blade (160) of the present example is operable to vibrate at ultrasonic frequencies in order to effectively cut through and seal tissue, particularly when the tissue is being clamped between clamp arm (44) and blade (160). Blade (160) is positioned at the distal end of an acoustic drivetrain that includes transducer assembly (12) to vibrate blade (160). By way of example only, the acoustic drivetrain may be configured in accordance with various teachings of various references that are cited herein.

In the present example, the distal end of blade (160) is located at a position corresponding to an anti-node associated with resonant ultrasonic vibrations communicated through a flexible acoustic waveguide, in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (44), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

II. Exemplary Breakaway Handle Assembly

Figure 2:
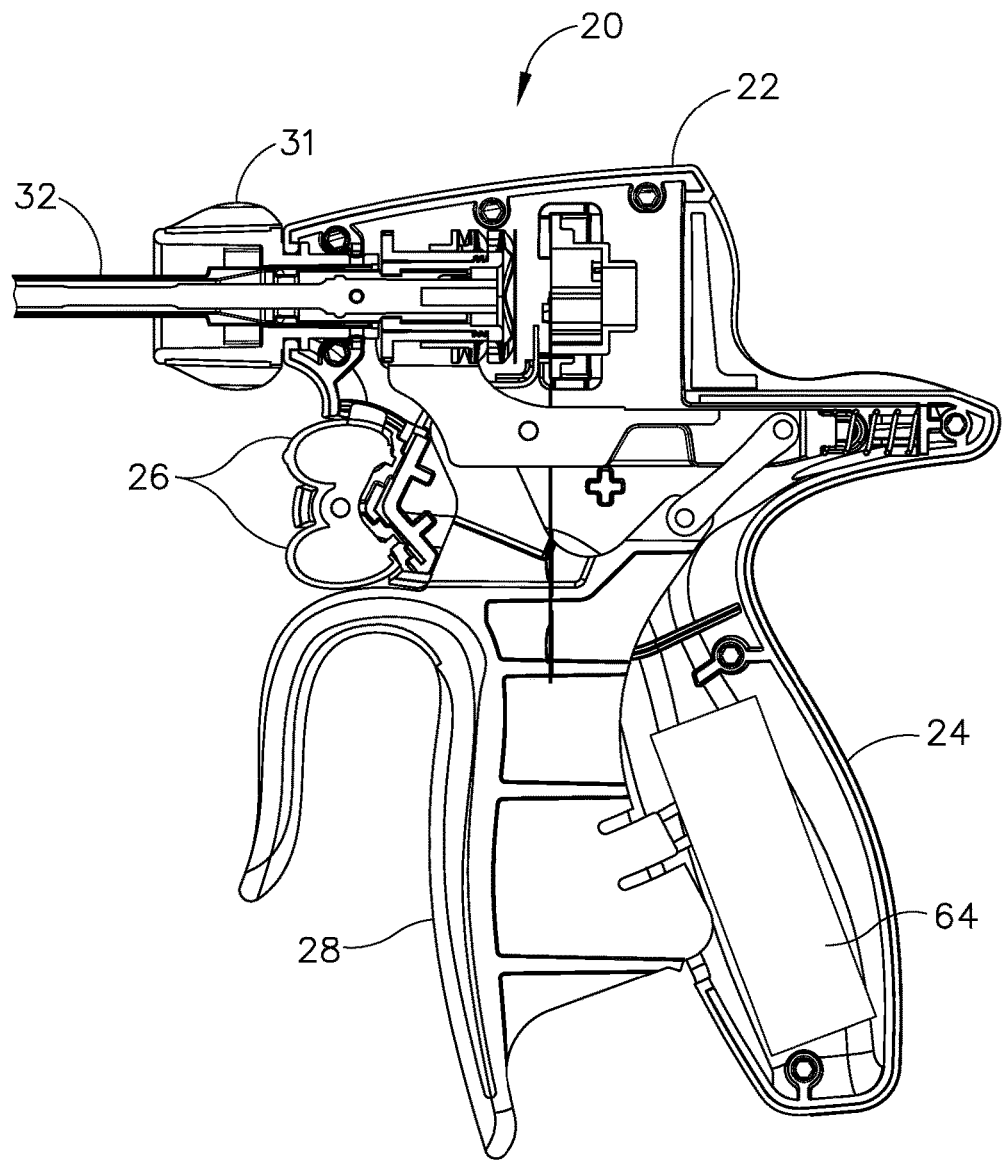
FIG. 2 depicts a cross sectional view of an exemplary alternative handle assembly for use with the instrument of FIG. 1.

In some versions, instrument (10) includes an integral power source within handle assembly (20) such that an external generator (16) is not needed. For example, FIG. 2 shows a battery (64) housed within grip (24) of handle assembly (20) that may be coupled with transducer assembly (12) to provide electrical power to transducer assembly (12). Examples of such integral power sources are described in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; U.S. patent application Ser. No. 13/804,417, entitled "Surgical Instrument with Selectable Integral or External Power Source," filed Mar. 14, 2013, published as U.S. Pub. No. 2014/0207124 on Jul. 24, 2014, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein. In some instances, it may be desirable to allow the user to dispose of battery (64) without contacting battery (64). For example, instrument (10) may include a breakaway handle assembly such that the user may grasp handle assembly (20) to dispose of battery (64) without contacting battery (64). The examples below include several merely illustrative versions of a surgical instrument with a breakaway handle assembly that may be readily introduced to an instrument (10).

A. Exemplary Breakaway Strip Assembly

Figure 3A:
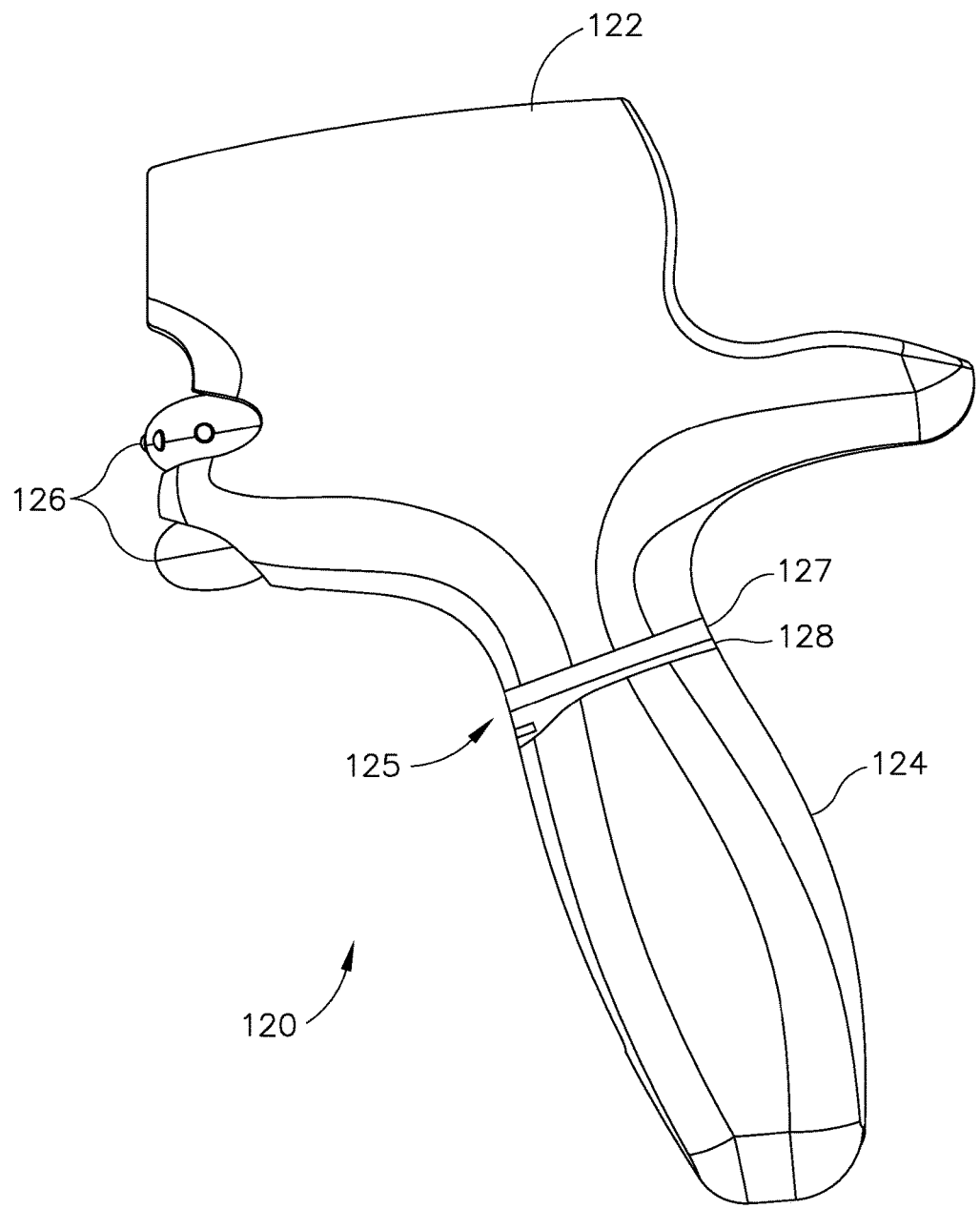
FIG. 3A depicts a side elevational view of another exemplary handle assembly for use with the instrument of FIG. 1.
Figure 3B:
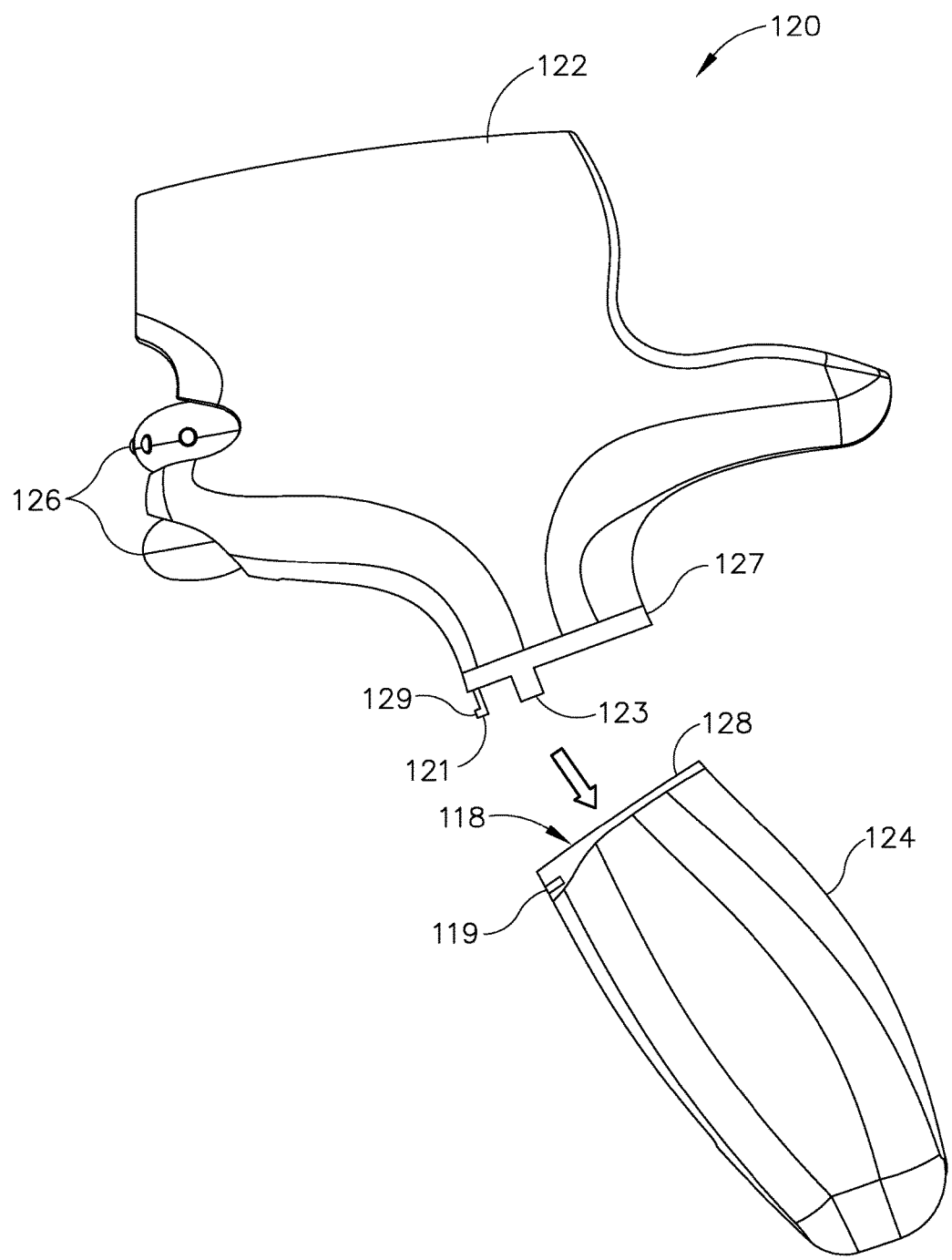
FIG. 3B depicts a side elevational view of the handle assembly of FIG. 3A, with the grip of the handle assembly removed.
Figure 3C:
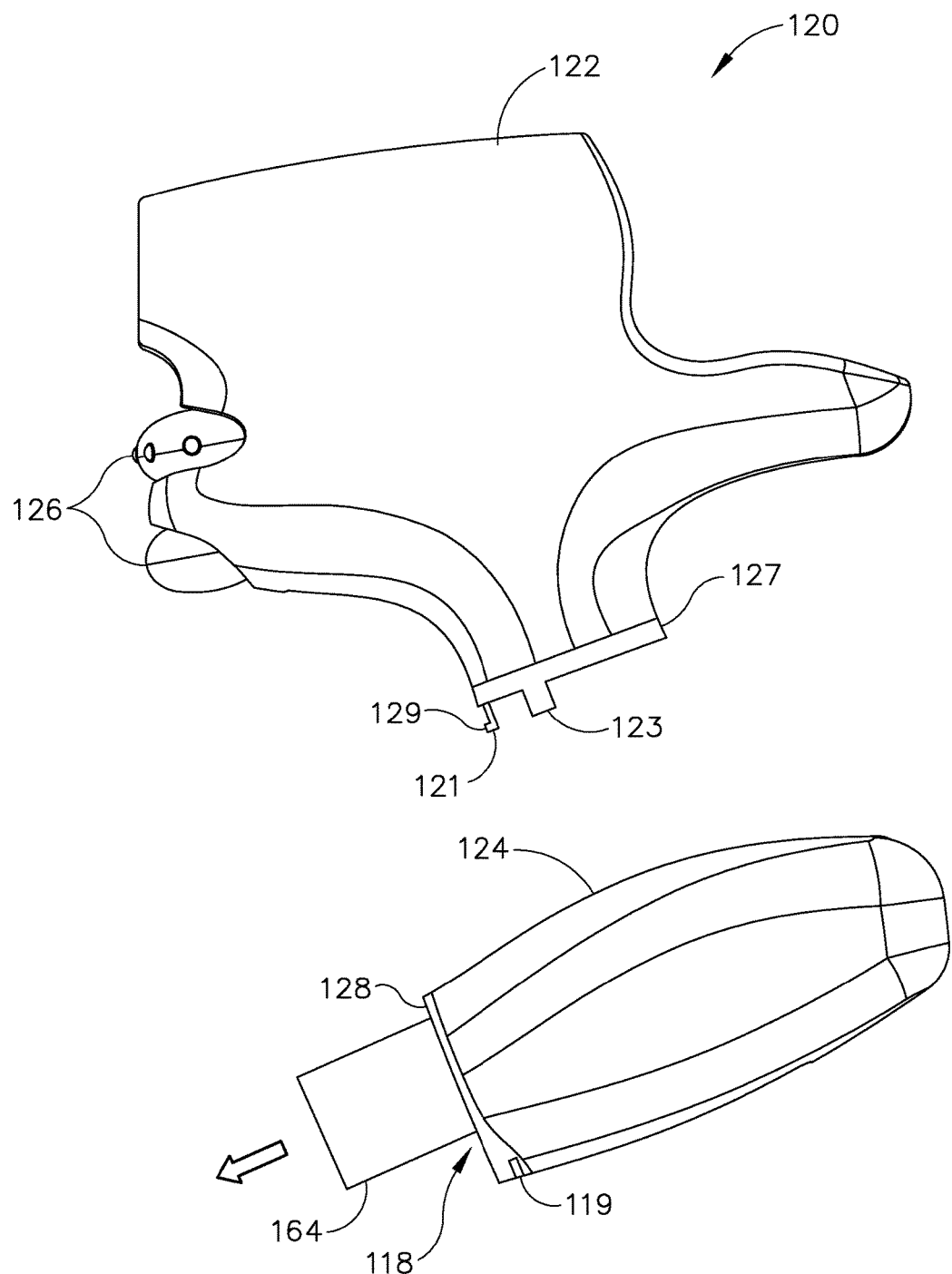
FIG. 3C depicts a side elevational view of the handle assembly of FIG. 3A, with the battery being removed.

FIGS. 3A-3C show an exemplary handle assembly (120) that is similar to handle assembly (20), except that body (122) of handle assembly (120) comprises a breakaway strip assembly (125). As best seen in FIG. 3A, strip assembly (125) is positioned between body (122) and grip (124). Strip assembly (125) comprises a first strip (127) that is coupled with body (122) and a second strip (128) coupled with grip (124). Strips (127, 128) are then releasably coupled together to thereby releasably couple body (122) with grip (124) of handle assembly (120). For example, FIG. 3B shows that first strip (127) comprises a distal tab (121) and a side tab (123) positioned on each side of distal tab (121). Tabs (121, 123) may be resiliently biased outwardly such that tabs (121, 123) secure first strip (127) relative to second strip (128) when first strip (127) is coupled with second strip (128). In the present example, distal tab (121) comprises a protrusion (129) extending distally on an end portion of distal tab (121). Second strip (128) defines an opening (119) on a distal portion of second strip (128) that is configured to receive protrusion (129) of first strip (127) to further secure first strip (127) with second strip (128) when first strip (127) is coupled with second strip (128). Although three tabs (121, 123) are shown in the present example, any other suitable number of tabs (121, 123) may be used to couple first strip (127) with second strip (128). Strips (127, 128) may be co-molded and made from an elastomeric material.

During a surgical procedure, strips (127, 128) are coupled to thereby couple body (122) with grip (124). First strip (127) is configured to couple with second strip (128) such that tabs (121, 123) secure first strip (127) with second strip (128), as shown in FIG. 3A. When strips (127, 128) are secured together, strip assembly (125) provides a fluid tight seal between body (122) and grip (124) such that strip assembly (125) prevents fluids from entering handle assembly (120) at the interface of strips (127, 128) or elsewhere at strip assembly (125). When body (122) is coupled with grip (124), tabs (121, 123) may flex slightly inwardly to slide through second strip (128) and press outwardly against second strip (128). Tabs (121, 123) thereby provide a friction fit to couple first strip (127) and second strip (128). When strips (127, 128) are coupled, protrusion (129) of distal tab (121) flexes outwardly through opening (119) of second strip (128) to further secure first strip (127) relative to second strip (128) through a snap fitting. In the present example, tabs (121, 123) are configured to press against second strip (128). However, tabs (121, 123) may also slide through second strip (128) such that tabs (121, 123) press against the inner walls of grip (124) to secure body (122) with grip (124). In some versions, tabs (121, 123) press against a portion of second strip (128) and a portion of grip (124). Opening (119) may also be positioned on grip (124) such that protrusion (129) of distal tab (121) slides within the wall of grip (124) instead of second strip (128). However, it should be noted that protrusion (129) is merely optional, such that the distal wall of distal tab (121) is used to press against second strip (128) and/or grip (124). Other suitable configurations for first and second strips (127, 128) will be apparent to one with ordinary skill in the art in view of the teachings herein.

When the surgical procedure is finished, a user may separate body (122) and grip (124), as shown in FIG. 3B. The user may press protrusion (129) of distal tab (121) inwardly to remove protrusion (129) from opening (119) of second strip (127). The user may then pull grip (124) away from body (122) such that tabs (121, 123) of first strip (127) slide out of second strip (128). Battery (164) is then exposed through an opening (118) on the top portion of grip (124). Grip (124) is then grasped and tipped downwardly to remove battery (164) from grip (124) through opening (118) by allowing battery (164) to slide out of grip (124) under the influence of gravity, as shown in FIG. 3C. Accordingly, grip (124) of handle assembly (120) may be used to dispose of battery (164) such that the user does not directly contact battery (164). Grip (124) may be used to dispose of battery (164) within a battery reclamation bin. Alternatively, battery (164) may be disposed of in any other suitable fashion.

B. Exemplary Pivoting Strip Assembly

Figure 4A:
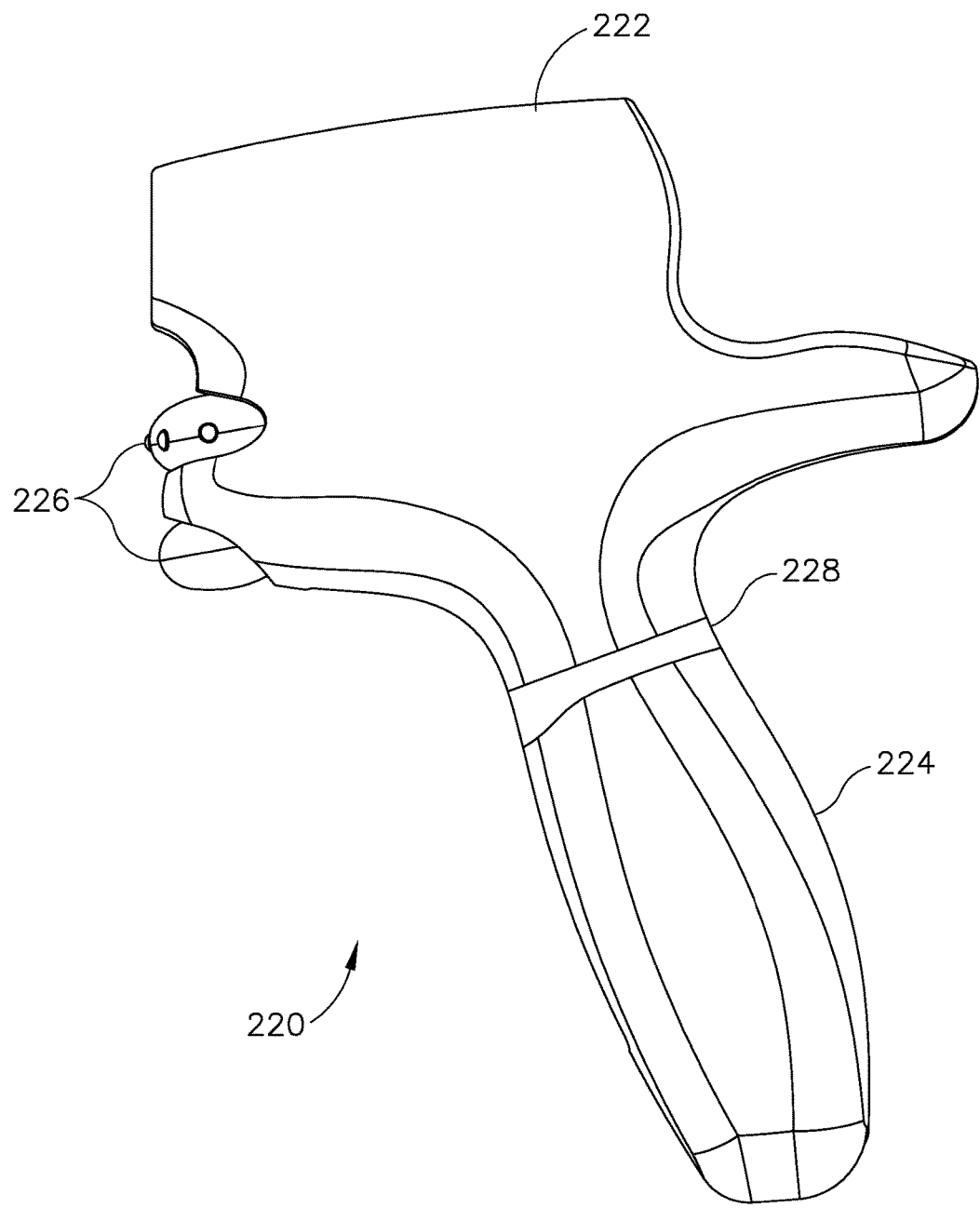
FIG. 4A depicts a side elevational view of another exemplary handle assembly for use with the instrument of FIG. 1.

FIGS. 4A-4B show another exemplary handle assembly (220) that is similar to handle assembly (120). However, instead of a breakaway strip assembly (125), handle assembly (220) comprises a strip (228) such that grip (224) may pivot relative to body (222) to dispose of a battery (264). As shown in FIG. 4A, strip (228) is positioned between body (222) and grip (224) to releasably couple body (222) with grip (224). When strip (228) is secured with body (222) and grip (224), strip (228) provides a fluid tight seal between body (222) and grip (224) such that strip (228) prevents fluids from entering handle assembly (220) at strip (228). Strip (228) comprises a proximal portion (229) that acts as a living hinge to allow grip (224) to pivot relative to body (222). Strip (228) may be co-molded with body (222) and/or grip (224). In some versions, strip (228) is made from an elastomeric material. In other versions, a proximal portion of strip (228) comprises a rigid material such that the rigid material provides a more supportive structure for strip (228). Other configurations for strip (228) will be apparent to one with ordinary skill in the art in view of the teachings herein.

During a surgical procedure, grip (224) is coupled with body (222) via strip (228), as shown in FIG. 4A. When the procedure is finished, a user may pull grip (224) away from body (222) to separate body (222) and grip (224), as shown in FIG. 4B. In the present example, proximal portion (229) of strip (228) acts as a living hinge such that grip (224) pivots relative to body (222). When grip (224) is pivoted relative to body (222), strip (228) may break apart such that a portion of strip (228) remains with grip (224) and a portion of strip (228) remains with body (222). Alternatively, strip (228) may remain in one piece to cleanly break apart from either grip (224) or body (222). While the present example shows grip (224) pivoting relative to body (222), it should be noted that grip (224) may further be entirely removed from body (222). Once grip (224) pivots away from body (222), a battery (264) is then exposed through an opening (218) on the top portion of grip (224). Grip (224) is then grasped and tipped downwardly to remove battery (264) from grip (224) through opening (218) by allowing battery (264) to slide out of grip (224) under the influence of gravity. Accordingly, grip (224) of handle assembly (220) may be used to dispose of battery (264) such that the user does not directly contact battery (264). Grip (224) may be used to dispose of battery (264) within a battery reclamation bin. Alternatively, battery (264) may be disposed of in any other suitable fashion.

C. Exemplary Peeling Strip Assembly

FIGS. 5A-5C show another exemplary handle assembly (320) that is similar to handle assembly (120), except that handle assembly (320) comprises a strip (327) positioned between body (322) and grip (324). Strip (327) comprises a tab (328). As shown in FIG. 5A, tab (328) is positioned on an end portion of strip (327) and has a larger width than strip (327). In the present example, strip (327) wraps around handle assembly (320) such that the other end of strip (327) contacts tab (328). Strip (327) thereby couples body (322) with grip (324), as shown in FIG. 5A. When strip (327) is secured with body (322) and grip (324), strip (327) provides a fluid tight seal between body (322) and grip (324) such that strip (327) prevents fluids from entering handle assembly (320) at strip (327). When a surgical procedure is finished, a user may grasp tab (328) of strip (327) to pull tab (328) away from handle assembly (320), as shown in FIG. 5B. Tab (328) is pulled to thereby pull strip (327) away from handle assembly (320) to separate strip (327) from body (322) and grip (324). As strip (327) is pulled away, grip (324) is separated from body (222) and battery (364) is exposed through an opening (318) in grip (324), as shown in FIG. 5C. Strip (327) may be fully removed from handle assembly (320) or strip (327) may be partially removed from handle assembly (320) to expose battery (364). Grip (324) is then grasped and tipped downwardly to remove battery (364) from grip (324) through opening (318) by allowing battery (364) to slide out of grip (324) under the influence of gravity. Accordingly, grip (324) of handle assembly (320) may be used to dispose of battery (364) such that the user does not directly contact battery (364). Grip (324) may be used to dispose of battery (364) within a battery reclamation bin. Alternatively, battery (364) may be disposed of in any other suitable fashion.

Although strip assemblies (125, 228, 327) have been described for a handle assembly (20, 120, 220, 320) of an ultrasonic device, such as instrument (10), it should be noted that the exemplary strip assemblies (125, 228, 327) could also be incorporated into other handle assemblies that comprise a battery (64, 164, 264, 364). For example, strip assemblies (125, 228, 327) may be added to handle assemblies of RF electrosurgical devices, surgical stapling devices, and/or other suitable surgical instruments. By way of example only, surgical instrument (10) may comprise an electrosurgical instrument constructed in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, now U.S. Pat. No. 8,939,974, issued Jan. 27, 2015; U.S. Pub. No. 2012/0116379, now U.S. Pat. No. 9,161,803, issued Oct. 20, 2015; U.S. Pub. No. 2012/0078243; U.S. Pub. No. 2012/0078247, now U.S. Pat. No. 9,402,682, issued Aug. 2, 2016; U.S. patent application Ser. No. 13/622,729, now U.S. Pat. No. 9,089,327, issued Jul. 28, 2015; U.S. patent application Ser. No. 13/622,735, now U.S. Pat. No. 9,545,253, issued Jan. 17, 2017; and/or U.S. patent application Ser. No. 13/658,784, now U.S. Pat. No. 9,421,060, issued Aug. 23, 2016. The disclosures of each of the foregoing references are incorporated by reference herein. Alternatively, surgical instrument (10) may comprise a surgical stapling and cutting instrument constructed in accordance with at least some of the teachings of U.S. Pat. No. 7,416,101; U.S. Pub. No. 2009/0209990, now U.S. Pat. No. 8,657,174, issued Feb. 24, 2014; U.S. Pub. No. 2012/0239012, now U.S. Pat. No. 8,453,914, issued Jun. 4, 2013; and/or U.S. patent application Ser. No. 13/716,308, now U.S. Pat. No. 9,445,816, issued Sep. 20, 2016. The disclosures of each of the foregoing references are incorporated by reference herein. Strip assemblies (125, 228, 327) may also be provided on a handle assembly (20, 120, 220, 320) to allow other components to be disposed of with grip (24, 124, 224, 324), in addition to, or in lieu of disposing of battery (64, 164, 264, 364) (e.g., control modules, printed circuit boards, etc.).

III. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument comprising:
   (a) an end effector operable to manipulate tissue;
   (b) a body, wherein a distal portion of the body is coupled with the end effector;
   (c) a grip, wherein the grip is configured to be grasped by a user's hand; and
   (d) a strip assembly transecting the body from the grip, wherein the strip assembly is configured to releasably couple the grip with the body;
   wherein the grip is movable from a first position to a second position, wherein the grip is coupled with the body in the first position, wherein the grip is configured to be detached from at least a portion of the body in the second position; and
   wherein at least a portion of the strip assembly is configured to detach from at least a portion of the grip, the body, or another portion of the strip assembly when the grip is in the second position.

2. The instrument of claim 1, wherein the grip is configured to house a battery.

3. The instrument of claim 2, wherein the grip is configured to expose the battery when the grip is in the second position.

4. The instrument of claim 3, wherein the battery is removable from the grip when the grip is in the second position.

5. The instrument of claim 1, wherein the strip assembly comprises an elastomeric material.

6. The instrument of claim 1, wherein the strip assembly comprises a tab on an end portion of the strip.

7. The instrument of claim 6, wherein the tab is configured to peel the strip assembly away from the instrument.

8. The instrument of claim 1, wherein the strip is configured to be fully detached from the body when the grip is in the second position.

9. A surgical instrument comprising:
(a) an end effector operable to manipulate tissue;
(b) a body, wherein a distal portion of the body is coupled with the end effector;
(c) a grip, wherein the grip is configured to be grasped by a user's hand; and
(d) a strip assembly transecting the body from the grip, wherein the strip assembly is configured to releasably couple the grip with the body;
wherein the grip is configured to decouple from at least a portion of the body at the strip assembly when the grip is pulled away from the body.

10. A surgical instrument comprising:
(a) an end effector operable to manipulate tissue;
(b) a body, wherein a distal portion of the body is coupled with the end effector;
(c) a grip, wherein the grip is configured to be grasped by a user's hand; and
(d) a strip assembly transecting the body from the grip, wherein the strip assembly is configured to releasably couple the grip with the body, wherein the strip assembly is actuatable to decouple at least a portion of the grip from the body.

11. The instrument of claim 10, wherein the strip assembly is configured to provide a fluid tight seal.

12. The instrument of claim 10, wherein the grip comprises a battery, wherein the grip is configured to dispose of the battery.

* * * * *